(12) United States Patent
Boone et al.

(10) Patent No.: US 8,449,623 B2
(45) Date of Patent: May 28, 2013

(54) SELF-ALIGNING PROSTHESIS WITH HYDRAULIC ACTUATORS

(75) Inventors: David Alan Boone, Seattle, WA (US);
Ben Gilbert Macomber, Shoreline, WA (US); Lonnie Love, Oak Ridge, TN (US)

(73) Assignees: Orthocare Innovations LLC, Oklahoma City, OK (US); UT-Battelle, LLC, Oak Ridge, TN (US)

( * ) Notice: Subject to any disclaimer, the term of this patent is extended or adjusted under 35 U.S.C. 154(b) by 31 days.

(21) Appl. No.: 12/886,380

(22) Filed: Sep. 20, 2010

(65) Prior Publication Data

US 2011/0160871 A1    Jun. 30, 2011

Related U.S. Application Data

(60) Provisional application No. 61/243,853, filed on Sep. 18, 2009.

(51) Int. Cl.
*A61F 2/60* (2006.01)
*A61F 2/74* (2006.01)

(52) U.S. Cl.
USPC .............................................. 623/26; 623/27

(58) Field of Classification Search
USPC .............................. 623/26, 27, 38, 43, 48, 53
See application file for complete search history.

(56) References Cited

U.S. PATENT DOCUMENTS

| | | | |
|---|---|---|---|
| 3,538,516 A | | 11/1970 | Bailey |
| 5,121,742 A | * | 6/1992 | Engen .............................. 602/16 |
| 6,517,585 B1 | * | 2/2003 | Zahedi et al. .................... 623/24 |
| 7,318,504 B2 | | 1/2008 | Vitale |
| 7,794,505 B2 | * | 9/2010 | Clausen et al. .................. 623/24 |
| 2006/0224247 A1 | * | 10/2006 | Clausen et al. .................. 623/24 |
| 2008/0139970 A1 | | 6/2008 | Macomber |
| 2008/0140221 A1 | * | 6/2008 | Macomber et al. ............. 623/27 |
| 2009/0054996 A1 | * | 2/2009 | Sykes et al. ..................... 623/24 |
| 2009/0204229 A1 | * | 8/2009 | Mosler et al. ................... 623/26 |
| 2010/0161077 A1 | | 6/2010 | Boone |
| 2010/0218626 A1 | | 9/2010 | Love |

OTHER PUBLICATIONS

International Search Report and Written Opinion mailed Dec. 27, 2010, issued in corresponding International Application No. PCT/US2010/049533, filed Sep. 20, 2010, 9 pages.

Schwerdtfeger, L.H., "The Involute Cam Rotary Actuator for Hydraulic Servomechanisms," Technical Report, Applied Physics Laboratory, Johns Hopkins University, Silver Spring, MD., Jul. 1958, 37 pages.

* cited by examiner

*Primary Examiner* — David Isabella
*Assistant Examiner* — Randy Shay
(74) *Attorney, Agent, or Firm* — Christensen O'Connor Johnson Kindness PLLC

(57) ABSTRACT

A hydraulic device includes a first plate that pivots in a first direction, a second plate that pivots in a second direction orthogonal to the first direction, a first hydraulic system comprising a first cylinder and piston, a second cylinder and piston and, channels connecting the first cylinder to the second cylinder, the first hydraulic system filled with hydraulic fluid, wherein the transfer of fluid between the first cylinder and second cylinder pivots the first plate, and a second hydraulic system comprising a third cylinder and piston, a fourth cylinder and piston and, channels connecting the third cylinder to the fourth cylinder, the second hydraulic system filled with hydraulic fluid, wherein the transfer of fluid between the third cylinder and fourth cylinder pivots the second plate.

7 Claims, 17 Drawing Sheets

US 8,449,623 B2

SELF-ALIGNING PROSTHESIS WITH HYDRAULIC ACTUATORS

CROSS-REFERENCE TO RELATED APPLICATION

This application claims the benefit of U.S. Provisional Application No. 61/243,853, filed Sep. 18, 2009, incorporated herein in its entirety by reference.

STATEMENT OF GOVERNMENT LICENSE RIGHTS

This invention was made with Government support under Grant No. 2R44HDO55709, awarded by The Department of Health and Human Services. The Government has certain rights in the invention.

BACKGROUND

Referring to FIG. 1, a conventional prosthesis 10 includes a prosthesis socket 60 into which the amputated limb is placed. The prosthesis socket 60 is connected to a prosthesis shank 30. The prosthesis shank 30 is further connected to a prosthesis foot 20, which bears the weight and makes contact with the ground. The conventional prosthesis 10 includes an adjustable connection, normally between the prosthesis socket 60 and the prosthesis shank 30. For example, the prosthesis shank 30 can have a coupling 40 with an upper end having a concave hemispherical surface. The prosthesis socket can have a pyramid adaptor 50 at the lower end thereof, which fits into an aperture provided in the concave surface of the coupling 40. The pyramid adapter 50 includes a surface curved to match the concave surface of the coupling 40. With this configuration, the prosthesis socket 60 can be articulated forward and backward and from side to side with respect to the prosthesis shank 30 and foot 20 to align the prosthesis socket 60 and prosthesis shank 30 to an optimal position that is both efficient and comfortable for the wearer of the prosthesis 10. Alignment can be described by a set of true angles that describe the tilt of the socket 60 with respect to a reference plane or the axis of the shank 30. One example of a reference plane is the plane that is perpendicular to the longitudinal axis of the shank 30. One angle is measured in the sagittal plane and the other angle is measured in the coronal plane A computerized prosthesis alignment system is disclosed in U.S. Patent Application Publication Nos. 2008/0139970 and 2008/0140221, incorporated herein expressly by reference for all purposes. These publications disclose a moment sensor 100 and control module 102 that is used to measure the moments occurring at the prosthesis socket. The moment sensor 100 can be attached to the socket and to the shank. As the prosthesis wearer walks using the prosthesis with moment sensor 100, the moments experienced in the anterior/posterior plane and the right/left plane are measured and recorded.

While the above-described computerized prosthesis alignment system is a significant advance in this art, new improvements are continuously being sought that enhance the experience for a prosthesis wearer to improve the comfort, lifestyle, and functionality.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

Disclosed is a device that automatically can rotate in the front-to-back and side-to-side directions to make adjustments to the spatial alignment of a prosthesis worn by a lower limb amputee patient.

A first embodiment is related to a hydraulic device. The device includes a first plate that pivots in a first direction, a second plate that pivots in a second direction orthogonal to the first direction, a first hydraulic system comprising a first cylinder and piston, a second cylinder and piston, and channels connecting the first cylinder to the second cylinder, the first hydraulic system filled with hydraulic fluid, wherein the transfer of fluid between the first cylinder and second cylinder pivots the first plate, and a second hydraulic system comprising a third cylinder and piston, a fourth cylinder and piston, and channels connecting the third cylinder to the fourth cylinder, the second hydraulic system filled with hydraulic fluid, wherein the transfer of fluid between the third cylinder and fourth cylinder pivots the second plate.

In the first embodiment, the first piston and the second piston may make contact with the first plate at locations diagonal to each other, and the third piston and the fourth piston may make contact with the second plate at locations diagonal to each other.

In the first embodiment, the first plate may have a first cam on which a shaft of the first piston rests and a second cam on which a shaft of the second piston rests, and the second plate may have a third cam on which a shaft of the third piston rests and a fourth cam on which a shaft of the fourth piston rests.

In the first embodiment, the first, second, third, and fourth cams may have a parabolic surface on which the respective shafts of the pistons rest.

In the first embodiment, the hydraulic device may further include a control device that blocks hydraulic fluid between the first cylinder and the second cylinder and a control device that blocks hydraulic fluid between the third cylinder and the fourth cylinder.

In the first embodiment, the hydraulic device may further include a middle block with two major surfaces and side surfaces separating the major surfaces, the first plate may have two dogs extending to two opposite side surfaces of the middle block and made to pivot therein, and the second plate may have two dogs extending to two opposite side surfaces of the middle block and made to pivot therein.

In the first embodiment, the hydraulic device may further include a central processing unit, an alignment unit, and a model, the hydraulic device receives signals of pressure or moments, compares the signals to the model, and sends signals to control devices that allow the transfer of hydraulic fluid between the first and second cylinders and between the third and fourth cylinders pivot the first and second plates to desired angles.

In the first embodiment, the hydraulic device may further include a middle block with two major surfaces, the first plate is placed alongside one of the major surfaces and the second plate is placed alongside the other of the major surfaces.

In the first embodiment, the hydraulic device may further include a middle block with two major surfaces separated by a thickness of the block, the hydraulic fluids of the first and second hydraulic systems are contained within the middle block.

In the first embodiment, the hydraulic device may further include a middle block with two major surfaces separated by a thickness of the block, the first cylinder and piston and the second cylinder and piston are inverted with respect to the third cylinder and piston and the fourth cylinder and piston.

In the first embodiment, the hydraulic device may further include a sensor to measure an angle of pivoting of the first plate and a sensor to measure an angle of pivoting of the second plate.

In the first embodiment, the hydraulic device may further include a first, second, third, and fourth pressure sensor to measure the pressure of the first, second, third, and fourth cylinders.

In the first embodiment, the hydraulic device may further include a first, second, third and fourth moment sensor placed over the first, second, third, and fourth cylinders.

A second embodiment is related to a method for aligning a prosthesis. The method includes attaching a hydraulic device to a prosthesis, receiving pressures or moments from sensors as a lower limb amputee walks using the prosthesis, the prosthesis comprises an aligned prosthesis socket described by a first true angle in a first plane and a second true angle in a second plane orthogonal to the first plane, comparing the pressures or moments to a model, the model describes the relationships between pressures or moments to first and second angles of an optimally aligned prosthesis, obtaining the variance between the received pressures or moments and the model, and converting the variance into a desired angle in the first plane and a desired angle in the second plane, the desired angles are calculated to reduce the variance between the received pressures or moments and the model, and commanding devices to transfer a hydraulic fluid from a high pressure cylinder to a low pressure cylinder to bring at least one true angle closer to a desired angle.

In the second embodiment, a driving force to transfer the hydraulic fluid may be provided by the force of the weight being supported by the prosthesis.

In the second embodiment, the method may further include sensing a true angle after commanding the devices and comparing a true angle to a desired angle.

In the second embodiment, the hydraulic device may remain rigid when no transfer of fluid is occurring.

In the second embodiment, the hydraulic device may pivot in the first plane when hydraulic fluid is transferred from a first cylinder to a second cylinder and may pivot in the second plane when hydraulic fluid is transferred from a third cylinder to a fourth cylinder.

A third embodiment is related to a method for changing the alignment of a lower limb prosthesis. The method includes providing a lower limb prosthesis with a hydraulic device having a first member that pivots in a first plane and a second member that pivots in a second plane orthogonal to the first plane, transferring hydraulic fluid from a first cylinder to a second cylinder of the hydraulic device, closing the distance between a first side of the first member and a first side of the second member when the hydraulic fluid is removed from the first cylinder that is located at the first side, and expanding the distance between a second side of the first member and a second side of the second member when the hydraulic fluid fills the cylinder located at the second side.

In the third embodiment, the method may further include transferring hydraulic fluid from a third cylinder to a fourth cylinder of the hydraulic device, closing the distance between a third side of the first member and a third side of the second member when the hydraulic fluid is removed from the third cylinder that is located at the third side; and expanding the distance between a fourth side of the first member and a fourth side of the second member when the hydraulic fluid fills the cylinder located at the fourth side.

In the above embodiments, a plate is one example of a pivot member; other pivot members may include blocks.

In the second and third embodiments, the methods may use any one of the hydraulic devices described in the first embodiment.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 3:
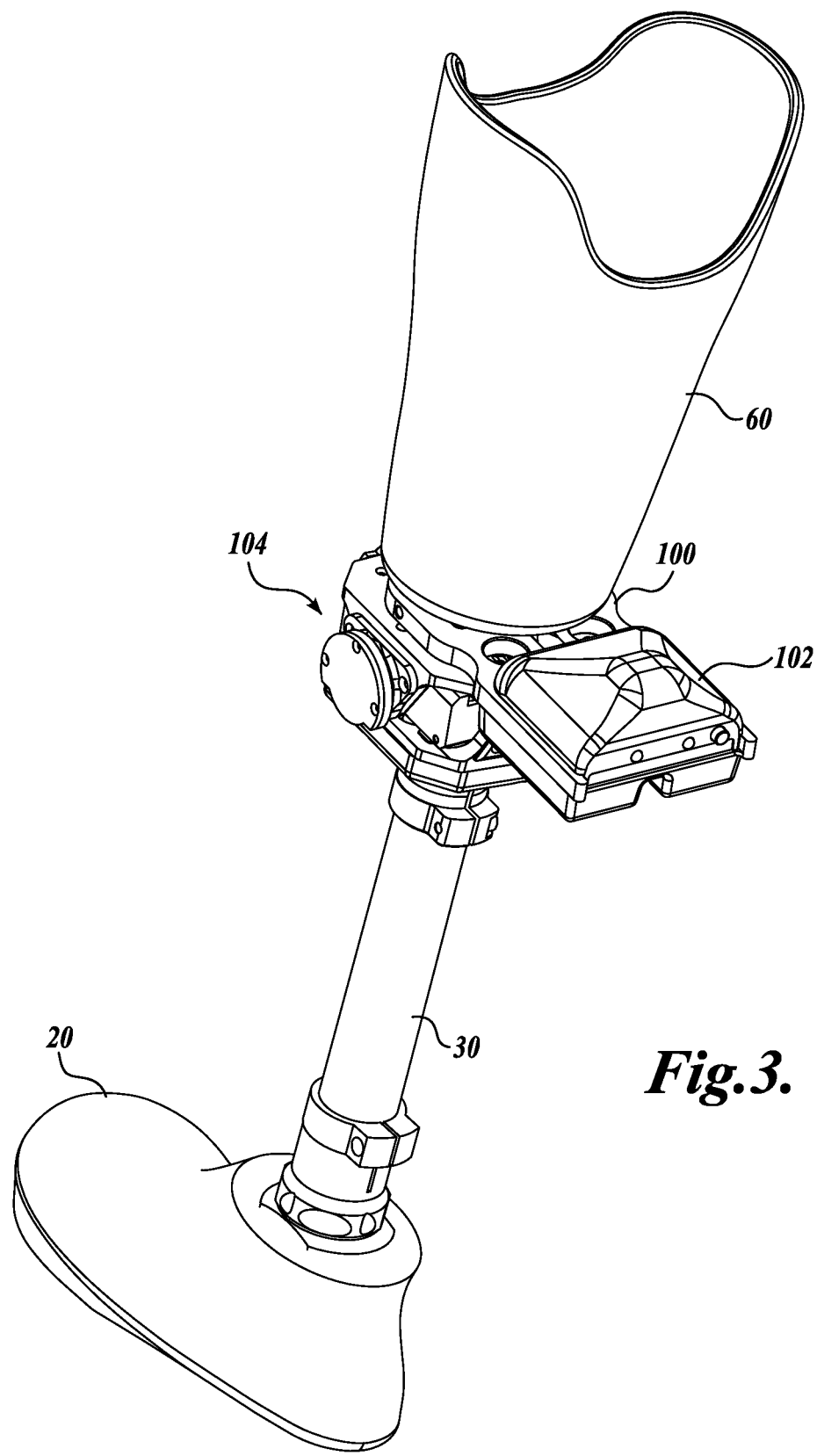
FIG. 3 is a diagrammatical illustration of a prosthesis including a moment sensor and hydraulic alignment device in accordance with one embodiment of the present invention.

Referring to FIG. 3, a hydraulic alignment device 104 is illustrated incorporated into a prosthesis. The moment sensor 100 is optional. The prosthesis includes a socket 60. The socket 60 is for receiving a residual limb of a lower limb amputee. The moment sensor 100 may optionally be placed underneath the bottom of the socket 60. If the moment sensor is not used, the socket 60 attaches to the hydraulic alignment device 104. The hydraulic alignment device 104 is attached to a shank 30, which in turn, is connected to a prosthesis foot 20. The moment sensor 100 includes an anterior beam, a posterior beam, a right and a left beam. Each beam further includes a first and second strain gauge attached to the side surface of the beam. Two sets of four strain gauges are arranged into two balanced bridges, each with a passive/resistive temperature component in series with each bridge so as to develop a voltage representative of the total bridge resistance. The orientation of the balanced bridges allows for calculation of moments into two orthogonal planes, such planes being the sagittal plane (anterior/posterior plane) and the coronal plane (right/left plane). The arrangement of the strain gauges in oppositely placed pairs reduces or eliminates the moments experienced along the third (transverse or horizontal) plane orthogonal to the other two. The upper side of the sensor 100 is attached to the bottom of the socket 20 and the bottom side of the sensor 100 is attached to the shank 60. For this purpose, the sensor 100 includes an inverted "pyramid" supported from a hemispherical dome. The sensor 100 rests on a concave matching cup of the shank and so provides articulation of the transverse plane, thus changing the spatial alignment between the socket 20 and the rest of the prosthesis. The moment sensor 100 also includes electrical components to power and convert voltage differences measured by the strain gauges into moments along both the coronal and sagittal planes. Also provided with the moment sensor 100 is a master unit 102. The master unit may include the power supply, radio transmitter, and/or any other type of wireless communication system, such as optical systems for transmitting and receiving data wirelessly to and from a computer.

Figure 4:
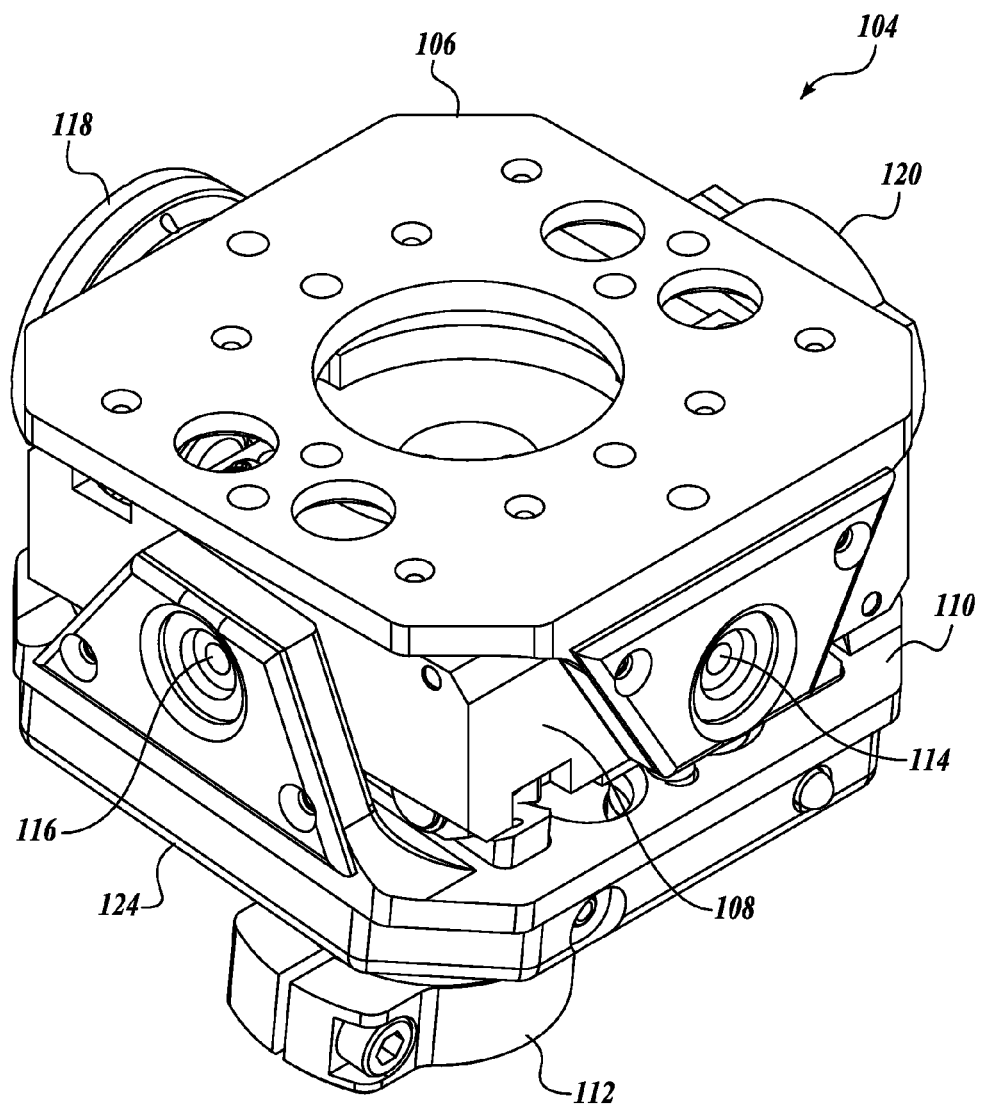
FIG. 4 is a diagrammatical illustration showing a hydraulic alignment device in accordance with one embodiment of the present invention.

Referring to FIG. 4, a hydraulic alignment device 104 is illustrated. The hydraulic alignment device 104 includes a top plate 106 to attach to the bottom of prosthesis socket 60 or if the moment sensor 100 is used, to the moment sensor 100. The hydraulic alignment device includes a middle block 108. The middle block 108 includes a first major side facing the top plate 106 and a second major side facing the bottom plate 110. The separation between the first major side and the second major side describe the thickness of the block 108 and is surrounded on four sides. The hydraulic alignment device includes a bottom plate 110. Top plate 106 and bottom plate 110 are considered pivot members in the present disclosure. Top plate 106 and bottom plate 110 are suited to pivot in directions orthogonal (at 90 degrees) to one another. The hydraulic alignment device includes a bottom case 124. The bottom case 124 includes a coupling 112 to attach to the shank 30. The top plate 106 may include a number of holes for attachment to the bottom of the socket 60 or the moment sensor 100. Other holes may be for ease of manufacturing or for assembling the hydraulic alignment device. The bottom place may also have holes for ease of assembling the various components of the hydraulic alignment device. The top plate 106 has two dogs projecting downwardly from two opposite sides. There are no dogs projecting from the remaining opposite sides. Each downwardly projecting dog is a pivot axis with respect to the middle block 108. The pivot axis 114 is opposite to the pivot axis 118, and independent therefrom, such that the axis pin of one side does not extend to the axis pin of the other side. Similarly, the bottom plate 110 includes upwardly projecting dogs on opposite sides, which are the sides that lack dogs on the upper plate 106. Also, the bottom plate 110 lacks dogs on the sides on which top plate 106 does have dogs. Each upwardly projecting dog is a pivot axis with respect to the middle block 108. The pivot axis 116 is opposite to the pivot axis 120, and independent therefrom, such that the axis pin of one side does not extend to the axis pin of the other side. With the construction as described above, the hydraulic alignment device 104 has a surface formed by the upper surface of the top plate that can move to any of the four sides in relation to a shank coupled to the bottom case 126. If a prosthesis socket is coupled to the top plate 106, then, the prosthesis socket can be moved to any of the four sides in relation to the shank. The amount of movement in any side direction may be described by an angle that the top surface of plate 106 makes with the plane perpendicular to the longitudinal axis of the shank (the reference plane). The alignment of the prosthesis, and particularly the alignment of the socket in relation to the shank may be described by a set of angles. These two angles are, one, the angle the top plate 106 makes with respect to the reference plane when viewed in the anterior/posterior (or sagittal) plane, and two, the angle the top plate 106 makes with respect to the reference plane when viewed in the right/left (or coronal) plane. The angles are a result of rotation along in the two perpendicular axes.

Figure 5:
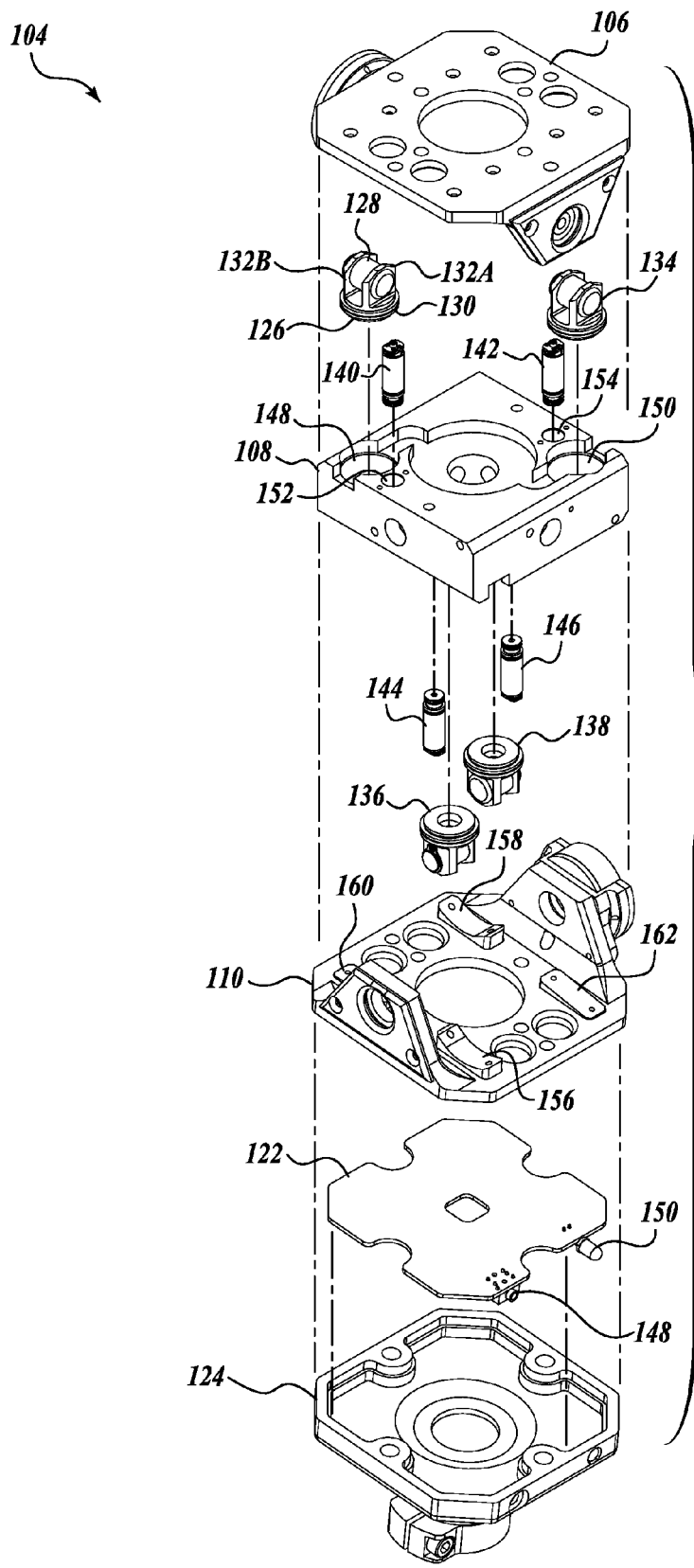
FIG. 5 is a diagrammatical illustration of an exploded view of the hydraulic alignment device of FIG. 4.

Referring to FIG. 5, an exploded view of the hydraulic alignment device 104 is illustrated. The middle block 108 includes four cylinder bores. Cylinder bores 148, 150, are seen from above placed on opposite corners of the block and two cylinder bores are placed from below on the remaining two opposite corners, but are not visible in FIG. 5. The middle block 108 also includes a pair of valves 140 and 142 that cause operation of the pistons 126 and 134. The valves 140 and 142 fit into valve cavities 152 and 154, respectively. A second pair of valves 144 and 146 cause operation of the pistons 136 and 138. The valves 144 and 146 also fit into valve cavities, but are not seen in FIG. 5. In one embodiment, the valves are solenoid valves that allow hydraulic fluid to pass through a piston or diaphragm from a high pressure side (the high side) to a lower pressure side (the low side). Solenoid valves can either be energized to open the valve or energized to close the valve. Alternative valves may include thermal valves, or other electromechanical valve. A first closed loop hydraulic system includes the pair of cylinder bores, the valve cavities 152, 154, and a system of connecting hydraulic fluid channels in the middle block 108. A second closed loop hydraulic system includes the pair of cylinder bores (from below), the valve cavities for valves 144 and 146 and a system of connecting hydraulic fluid channels in the middle block 108. Closed loop means that the volume of hydraulic fluid in the system remains a constant volume and no other hydraulic fluid is brought into the system or removed from the system with the exception of a small accumulator to offset thermal expansion and leaks of hydraulic fluid. However, hydraulic fluid can be transferred between the pair of cylinders of each hydraulic system. The bore 148 receives a piston 126. The bore 150 receives a piston 134. Pistons 126 and 134 cooperate to change a first of the two angles (i.e., cause rotation) by allowing hydraulic fluid to be transferred from one cylinder to the other. One cylinder is emptied of hydraulic fluid causing the piston to lower, while at the same time the opposite diagonal cylinder is filled with hydraulic fluid causing the piston to rise. As is apparent, the filling and emptying of cylinders on opposite diagonal corners will cause one side to be lower that the other side. This is also described by imaging the plane made by the top plate 106 will rotate several degrees. Pistons 136 and 138 cooperate to change a second of the two angles (i.e., cause rotation) by allowing hydraulic fluid to be transferred from one cylinder to the other. One cylinder is emptied of hydraulic fluid causing the piston to lower, while at the same time the opposite diagonal cylinder is filled with hydraulic fluid causing the piston to rise. As is apparent, the filling and emptying of cylinders on opposite diagonal corners will cause one side to be lower that the other side because the introduction of hydraulic fluid into a cylinder will push a respective piston further out of the cylinder and push the respective top 106 and bottom 110 plates further apart from one another. This motion is also described by viewing the plane made by the top surface of the top plate 106 rotate several degrees.

The piston 126 includes a pair of piston rings 130, a first and second connecting rod 132A and 132B, and a shaft 128 captured between the connecting rods 132A and 132B. The remaining pistons 134, 136, and 138 have similar components as piston 126. The pistons 126 and 134 face downwardly while pistons 136 and 138 face upwardly. Further, pistons 126 and 134 have their shafts aligned parallel to one another, and the shafts of pistons 136 and 138 are parallel to one another, but perpendicular to the shafts of pistons 126 and 134. As can be appreciated, when the shafts of pistons 126 and 134 are perpendicular to the shafts of pistons 136 and 138, each hydraulic system will operate to adjust one of two angles described above. Further, because each of the two hydraulic systems may be operated independent of the other, one hydraulic system can be rigid by preventing hydraulic fluid to flow, while the other hydraulic system is allowed to flow hydraulic fluid between cylinders to change the amount of angle. Both hydraulic system can remain rigid, and the prosthesis is held rigid as well.

Referring to the bottom plate 110, the shafts of pistons 136 and 138 ride on cams 156 and 158, respectively, placed on the upperside of the bottom plate 110. The wedges 160 and 162 are to support the middle block 108 when tilted to that side and to prevent deformation of the block 108. Similarly, the shafts of pistons 126 and 134 ride on cams (which are not seen) attached on the underside of the upper plate 106. Therefore, as can be appreciated, the load supported by the upper plate is transferred through the cam surfaces (not seen) to the piston shafts and pistons causing a certain amount of pressure in cylinders 148 and 150. Similarly, the force on the bottom plate 110 is transferred from the cam surfaces 156 and 158 to the piston shafts and pistons 136, 138 causing a certain amount of pressure in the cylinders. The forces applied at the four corners of the hydraulic alignment device are rarely if ever equal when used for walking in a prosthesis, which means the pressures on the four cylinders are different. The uneven pressures can be used as the driving force to move the hydraulic fluid from one cylinder to the other. Further, the pressures inside the four cylinders can be measured using pressure sensors and used to calculate whether the prosthesis is in alignment or to detect and make corrections in the alignment to assist the prosthesis wearer such as when walking on uneven surfaces.

As can be appreciated from the description above, the top plate 106 may be caused to pivot relative to the middle block 108 in a first plane and the bottom plate 110 may be caused to pivot relative to the middle block 108 and in a direction orthogonal to the first plane in a second plane. When the hydraulic alignment device 104 is used on a prosthesis, these two planes can be made to correspond with the coronal and sagittal planes of the human anatomy. Matching the pivoting action of the hydraulic alignment device with the planes of the human anatomy allows for alignment because the angles in the two planes can be based on the reliance that the two angles are aligned with the sagittal and coronal planes. Because the hydraulic alignment device may be placed between the socket and shank of a prosthesis, it is readily appreciated that the hydraulic alignment device 104 provides for spatial alignment of the prosthesis in two orthogonal planes (sagittal and coronal).

Below the bottom plate 110, a printed circuit board 122 is provided that includes electronic components, including a central processing unit, a memory device, a power supply, and connections to power each of the valves 140, 142, 144, and 146. In an alternative embodiment, the printed circuit board 122 could be placed within a cavity in the middle block. A jack or port 148 may be provided for any number of functions, such as to connect to a battery charger, and/or to provide for information upload and transfer. An LED status light 150 may provide an indicator to notify that the device is operational. The bottom case 124 encases the electronic printed circuit board to protect the electrical components. The bottom case 124 also has the coupling 124 made to couple to the prosthesis shank.

Figure 6:
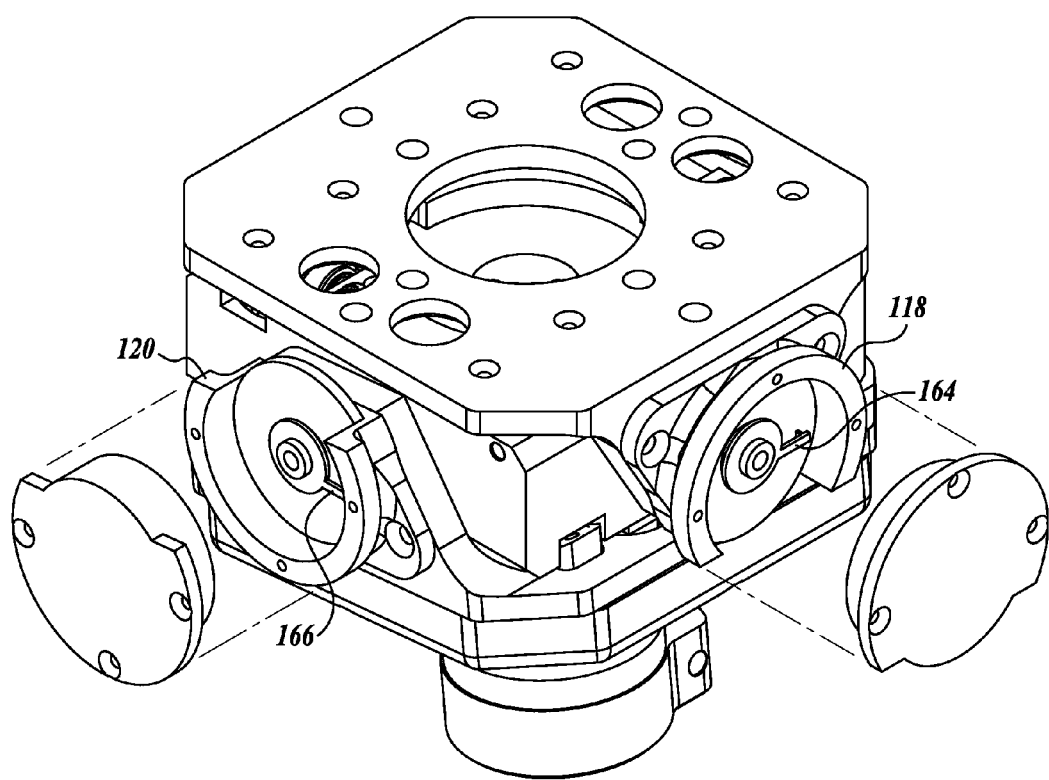
FIG. 6 is a diagrammatical illustration of the hydraulic alignment device of FIG. 4 rotated 180 degrees.

As discussed above, the top and bottom plates articulate in orthogonal planes, whose movements can be described as a set of angles. FIG. 6 is an illustration of the hydraulic alignment device 104 showing an angle sensor 164 placed at one of the pivot points 118 and a second angle sensor 166 placed at the pivot point 120 that is at ninety degrees from the pivot point 118. Each of the angle sensors 164 and 166 provide an indication of the angle being formed by the top surface of the top plate and the lower surface of the bottom plate or the reference plane. The angle sensors 164 and 166 may include a potentiometer. The measurement of angles in each plane is used to determine whether or not the correction of alignment has been achieved as further described below.

Figure 7:
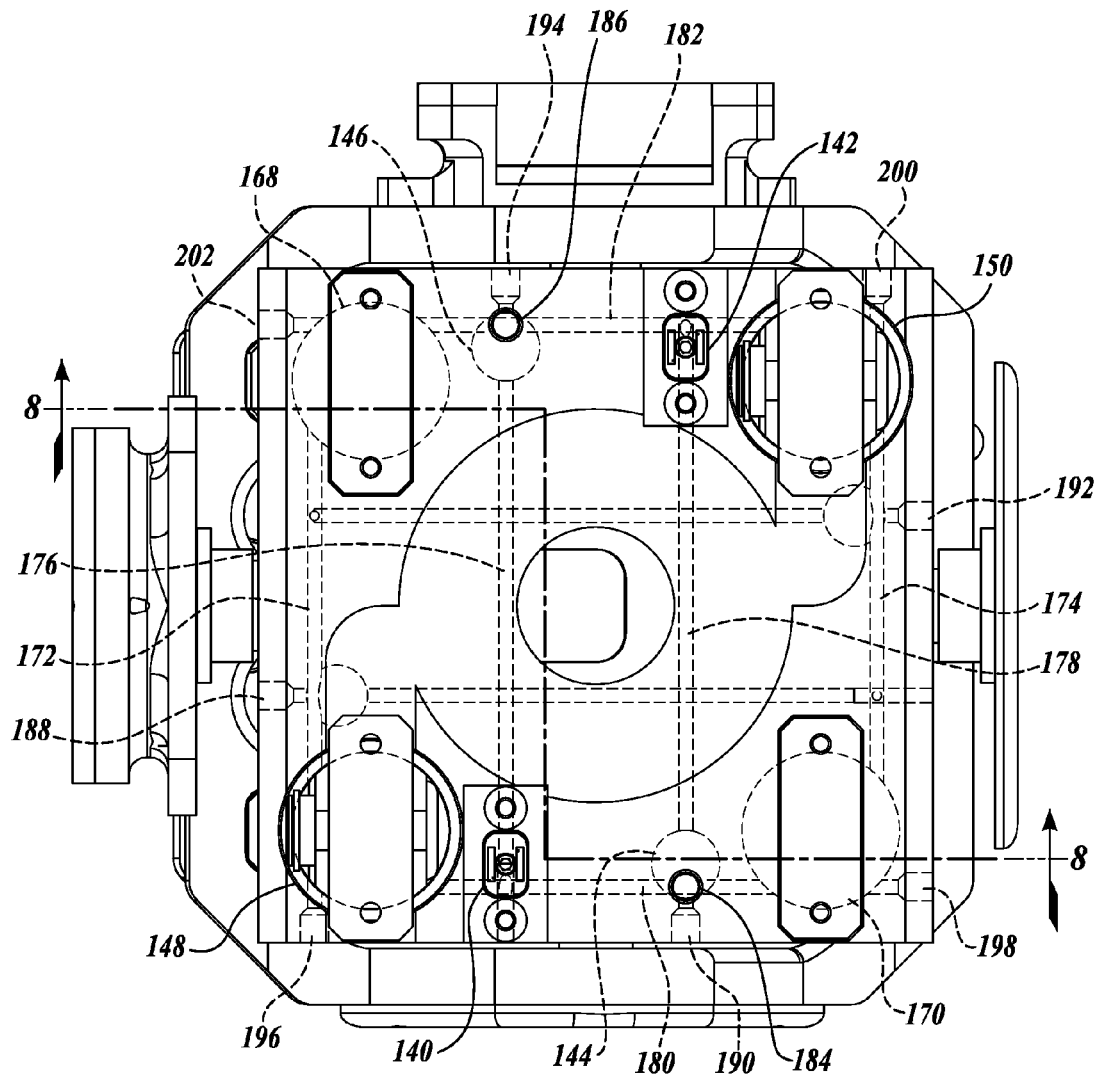
FIG. 7 is a diagrammatical illustration of a top plan view of a hydraulic alignment device with a top plate removed to show the internal hydraulic fluid channels.

Referring to FIG. 7, a diagrammatical illustration of a top plan view of the hydraulic alignment device 104 is shown illustrating the configuration of the two closed loop hydraulic systems. The dotted lines represent channels within the middle block 108 for hydraulic fluid. It is apparent that other configurations are possible, the configuration being shown here is intended to be representative. The volume of each closed loop hydraulic system includes the space above the piston in each cylinder, the volume within the valve cavities excluding the valve itself, and the volume of the connecting channels between the two cylinders and valves. A first hydraulic system is formed by cylinders 148, 150, valves 142, 144, and channels 180, 178, 176, 182, 184, and 186. A second closed loop hydraulic system is formed by cylinders 168, 170, valves 144, 146, and channels 172, 174, 192, 188, and two vertical channels that are not visible in FIG. 7. To illustrate the construction of a hydraulic system, the first hydraulic system will be described in detail. The second system being similar to the first except for being oriented on the opposite major side of the middle block 108. The cylinders 126, 134, 136, and 138 have an opening above the maximum reach of the pistons. Hydraulic fluid fills the cylinders and is transferred into and out of the cylinder by the same channel. A valve may be constructed with a dual acting piston, meaning that one side of the piston is in communication with and sees the pressure of a first cylinder in a pair, such as cylinder 126, and the other side of the piston is in communication with and sees the pressure in the second cylinder of a pair, such as cylinder 134. The valves can be actuated to prevent hydraulic fluid movement, thus locking the pistons from moving within cylinders 126 and 134, and the hydraulic alignment device 104 remains rigid. In one embodiment, horizontal and vertical channels are used to create the interconnecting channels between cylinders and valves. Horizontal channels of the first system include 180, 182, 176, and 178. Channels may be bored at different depths to avoid other features. Channel 180 is bored starting from the plug 198 and ends at the cylinder 148 and passes through the cavity of valve 140. Channel 182 is bored starting from the plug 202 and ends at the cylinder 150 and passes through the cavity of valve 142. Vertical channel bored at 184 intersects the horizontal channel 180. Vertical channel bored at 186 intersects the horizontal channel 182. Horizontal channel 178 is bored starting at plug 190 and ends at cavity of valve 142 at a lesser depth than channel 182. Horizontal channel 178 intersects the vertical channel 184. Horizontal channel 176 is bored starting at plug 194 and ends at cavity of valve 140 at a lesser depth than channel 180. Horizontal channel 176 intersects the vertical channel 186. A similar construction is used to connect cylinders 168, 170 to valves 144, 146.

Figure 1:
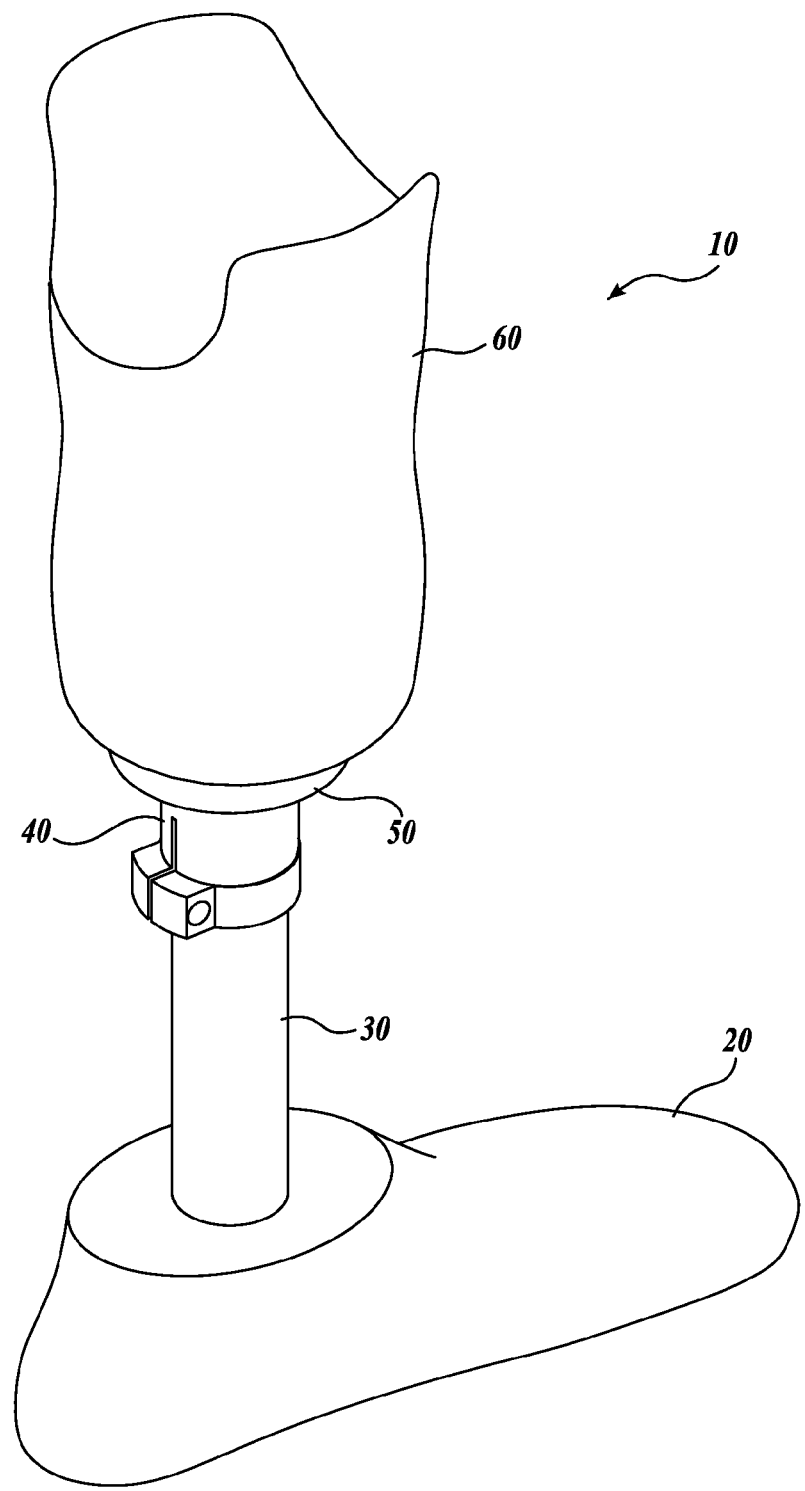
FIG. 1 is a diagrammatical illustration of a prosthesis including the socket, shank, and foot.
Figure 2:
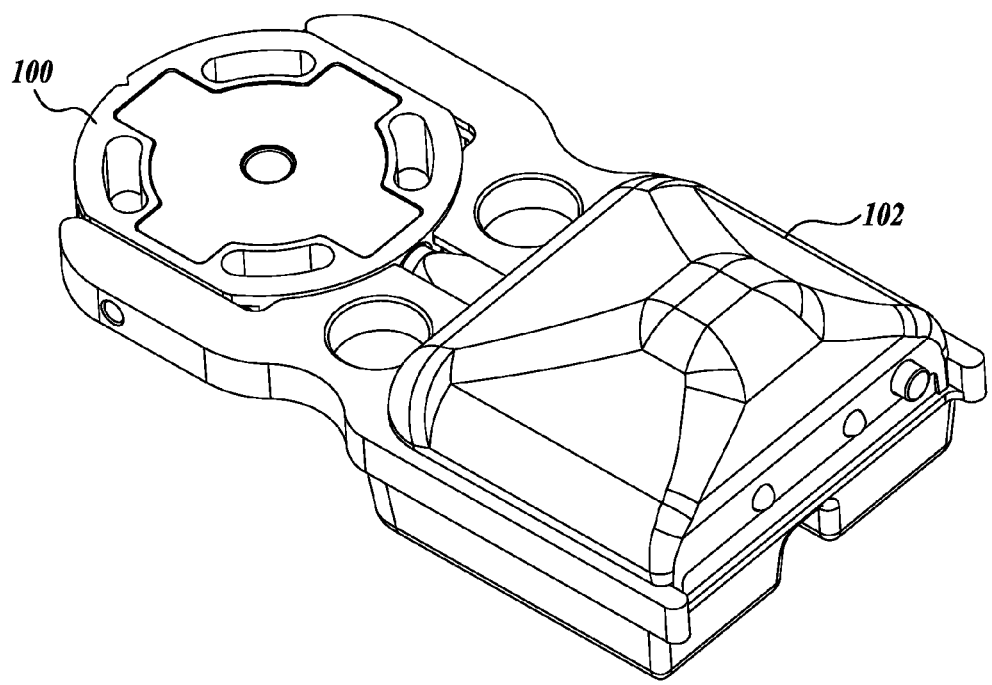
FIG. 2 is a diagrammatical illustration of a moment sensor.
Figure 14:
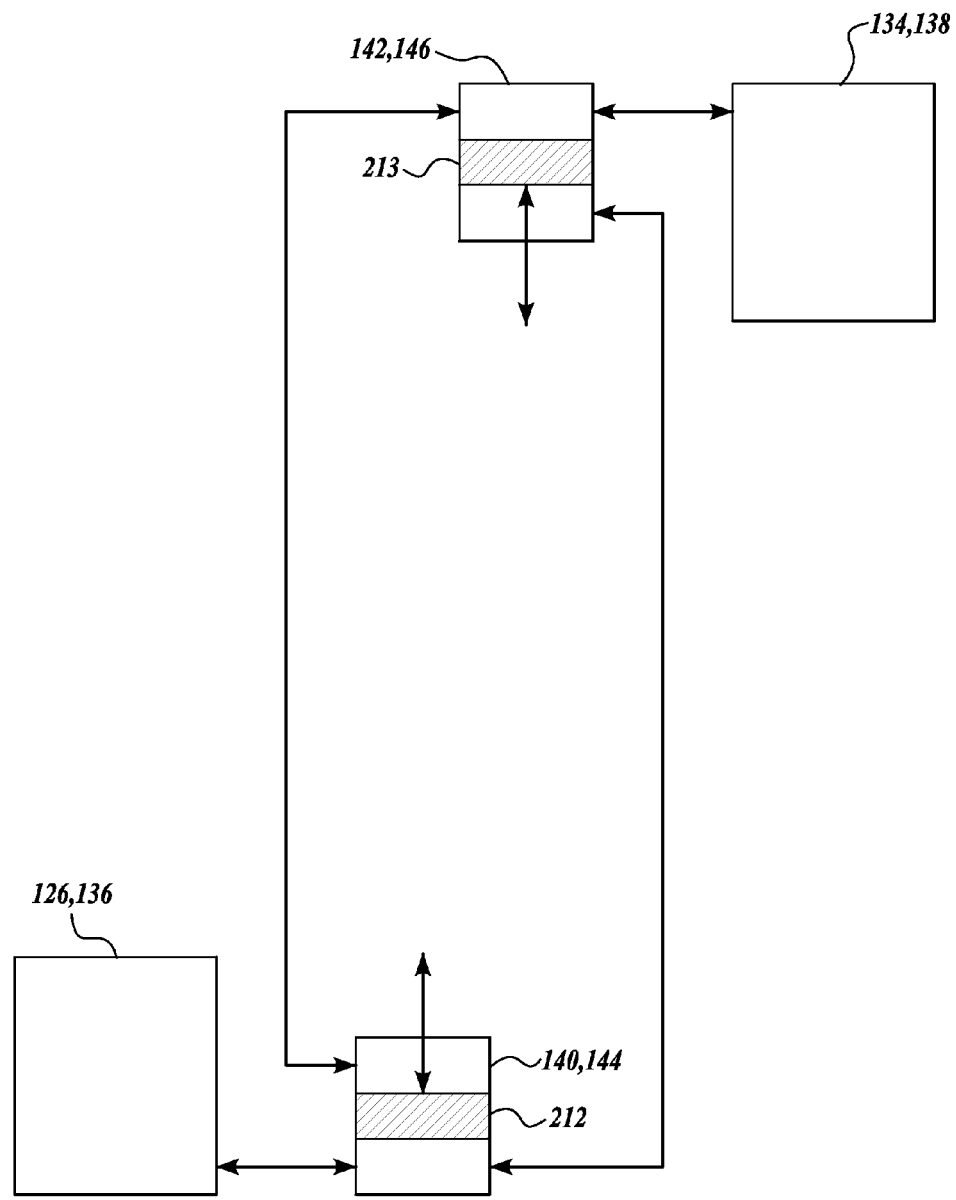
FIG. 14 is a schematic of the closed loop hydraulic system for a pair of cylinders in accordance with one embodiment of the present invention.

As described above, it can be appreciated that a hydraulic system includes a horizontal channel that connects a cylinder to a valve cavity at a first location, which then continues and connects to a vertical channel, which then connects to a horizontal channel and ends at a second location at a second valve cavity. A simplified schematic of the hydraulic system is illustrated in FIG. 14. Using the cylinders 126, 134, and valves 140, 142 as representative, a first cylinder 126 connects to high side of a valve piston of a first valve 140 and also connects to the low side of a valve piston of a second valve 142. The second cylinder 134 connects to the high side of a valve piston of the second valve 142 and also connects to the low side of the valve piston of the first valve 140. The valve pistons 212 and 213 may oscillate up and down as shown by the arrows to allow transfer of hydraulic fluid from the high side to the low side depending on which cylinder has the higher pressure. The pistons and cylinder pairs 126, 134 and 136, 138 come under repeated loads when the amputee steps on the prosthesis. During this phase of walking, the pressure in the hydraulic systems can rise to over 2,000 pounds per square inch. This pressure provides the driving force for moving the hydraulic fluid from one cylinder to the other, thus, avoiding the need to have pumps to propel the hydraulic fluid through the system. The valves 140, 142, 144, and 146 can be pulse shift valves that move in small increments. When the valves are not energized, the hydraulic alignment device 104 should be rigid, not allowing the transfer of hydraulic fluid into and out of any cylinder and/or valve. Each individual cylinder 126, 134, 136, and 138 may experience a different pressure when the device 104 is rigid, because each cylinder is placed at a corner of the device and may experience different forces. The pressures in the cylinders 126, 134, 136, and 138 may be measured. These pressures can be correlated to moments experienced by the prosthesis socket. This is an alternative to measuring the moments using the moment sensor 100 illustrated in FIG. 2. In another embodiment, a strain gauge can be placed at each of the cylinder heads (on the middle block 108) and used to measure the bending moments acting on the prosthesis by measuring the pressure acting on the cylinder heads. Pressure or moments may be used to measure the different forces affecting the prosthesis. Pressure and bending moments can be correlated to an ideally aligned prosthesis by comparing the current readings against the pressure and bending moments of a plurality of prosthesis wearers with known good alignment.

Figure 8:
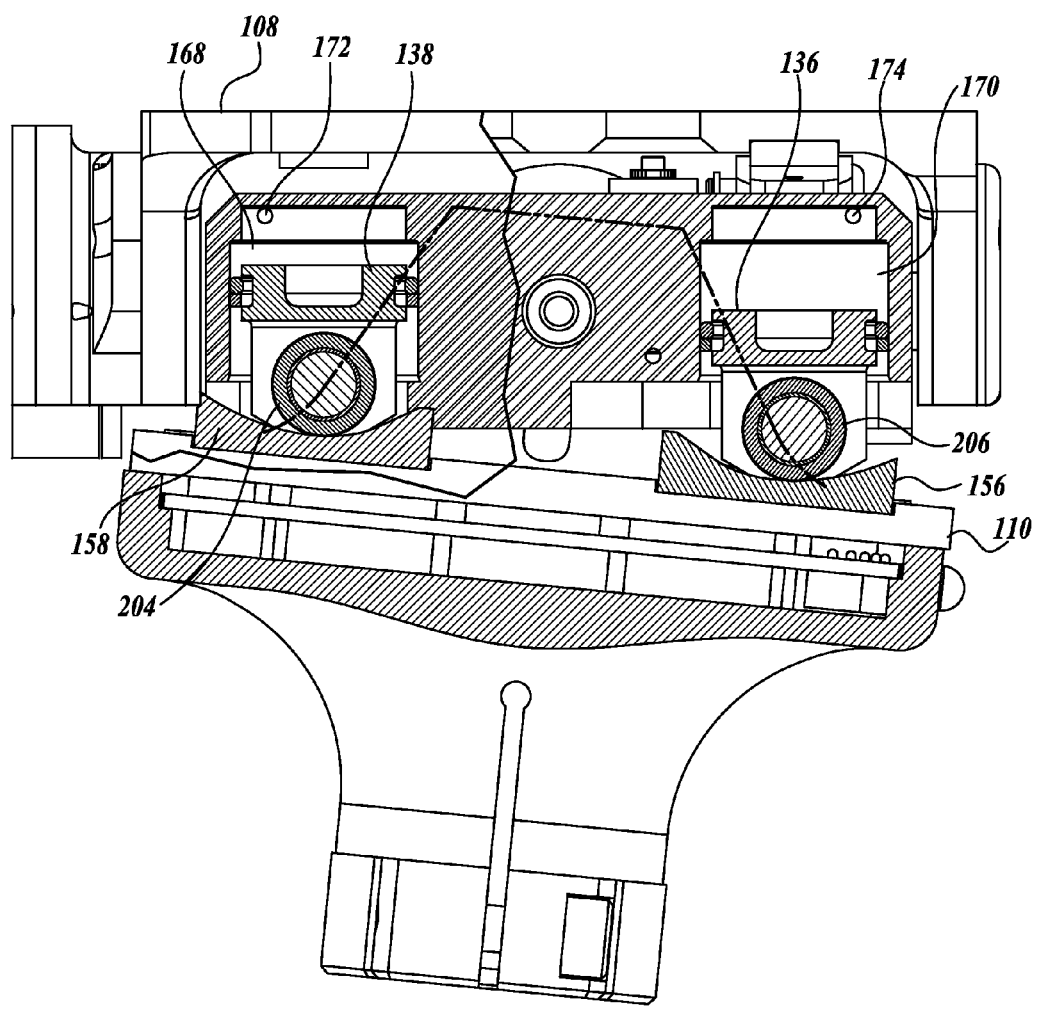
FIG. 8 is a diagrammatical illustration of a multi cross-sectional view of the hydraulic alignment device of FIG. 7.

Referring to FIG. 8, a multi cross-sectional view of the hydraulic alignment device 104 is illustrated to show the action of the pair of pistons. While the description below is with respect to cylinders 168 and 170, it should be understood that the action of cylinders 148 and 150 is similar, except for being inverted in the device and causing pivoting in a direction orthogonal to the pivoting direction caused by cylinders 168 and 170, i.e., the pivoting direction caused by the action of cylinders 148 and 150 is at 90 degrees with respect to the pivoting direction caused by cylinders 168 and 170.

Cylinders 168 and 170 are illustrated. Each cylinder 168 and 170 has an opening 208 and 210, respectively, for the introduction or removal of hydraulic fluid from the cylinder. Piston 138 is at the top of movement within cylinder 168, which causes the middle block 108 to move closer to the lower plate 110, while piston 136 is at the bottom of movement within cylinder 170, which causes the middle block 108 to move away from the lower plate 110. As can be appreciated, this causes a rotation about the pivot axis and changes the angle of the lower plate 110 with respect to the middle block 108. A similar operation is carried out with cylinders 148 and 150 except for being in a direction at 90 degrees and causing the angle of the upper plate 106 to change with respect to the middle block 108. Piston shafts 204 and 206 travel on cams 158 and 156. The cams' 158, 156 upper surfaces form a parabolic shape. A parabolic shape is described by a curve whose points are equidistant from a focus point and directrix line. The axis of symmetry of a parabola passes through the focus point and the vertex point on the parabola. The shape of the upper cam surfaces can be described by a parabola whose vertex is at the middle of the upper cam surface. When the hydraulic alignment 104 is level (i.e., the top plate 106 is parallel with the bottom plate 110), the piston shafts rest on the middle of the upper cam surface (i.e., the vertex of the parabola). When hydraulic fluid is added to a cylinder, the piston moving down will move inwardly on the cam surface, and when hydraulic fluid is removed from a cylinder, the piston moving up will move outwardly on the cam surface. The parabolic surface of the cams is advantageous in this respect as the parabolic shape defines a movement of the piston such that the force applied to the piston is parallel with the cylinder bore.

Figure 9:
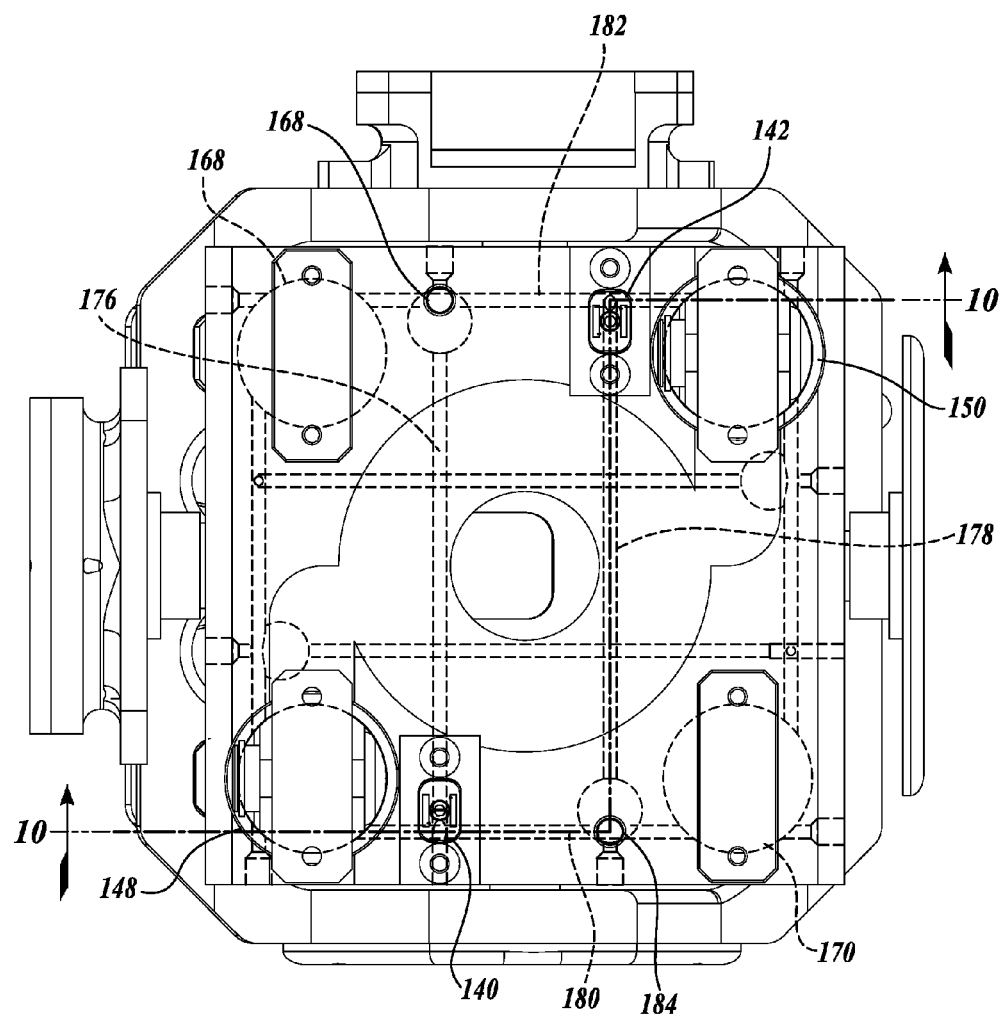
FIG. 9 is a diagrammatical illustration of a top plan view of a hydraulic alignment device with a top plate removed to show the internal hydraulic fluid channels.
Figure 10:
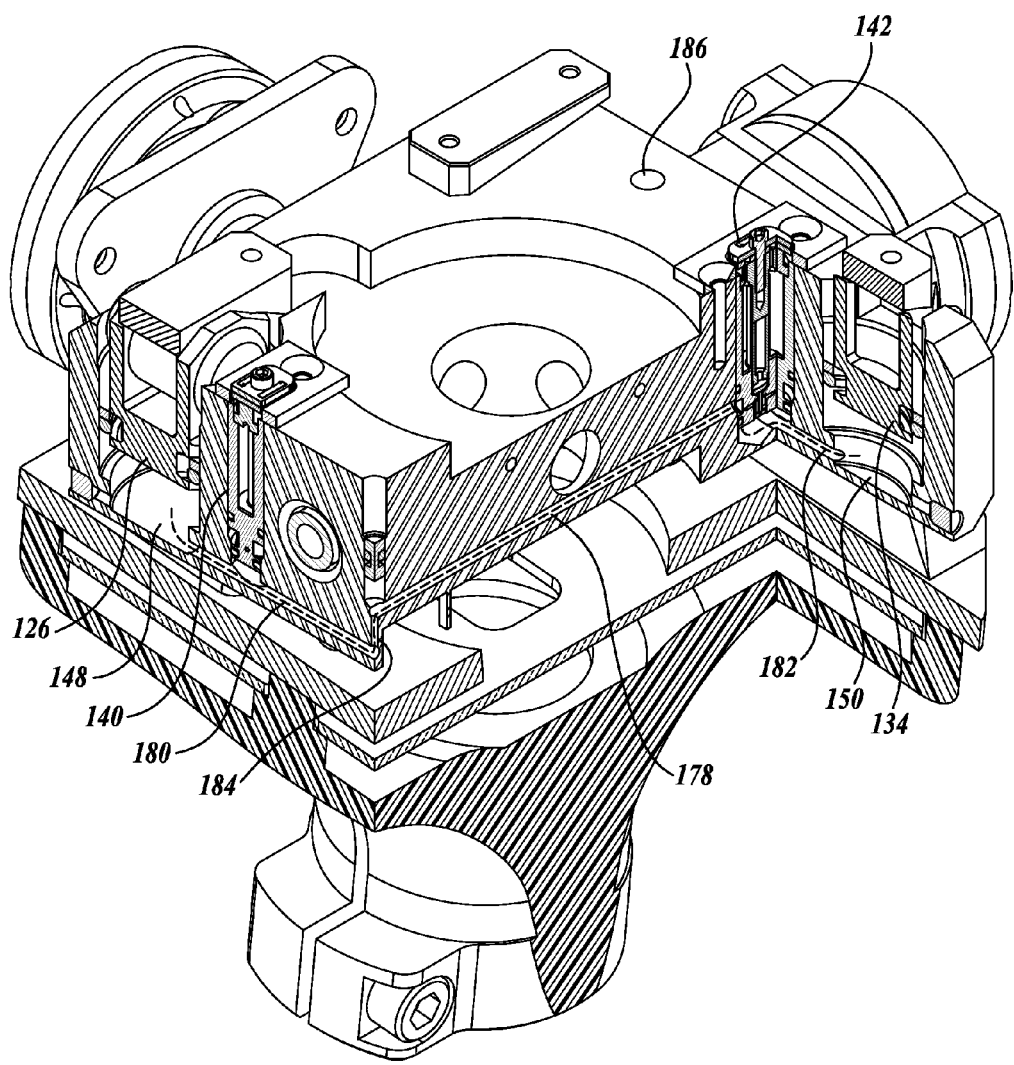
FIG. 10 is a diagrammatical illustration of a perspective multi cross-sectional view of the hydraulic alignment device of FIG. 9.

Referring to FIGS. 9 and 10, a top plan view and a multi cross-sectional view are illustrated to better understand the construction of the hydraulic systems. In FIG. 9, a cross-sectional view is taken along the cylinder 148, the channel connecting cylinder 148 to the valve 140 cavity, the horizontal channel 180, the vertical channel 184, the horizontal channel 178, the valve 142 cavity, and a portion of the channel 182 connecting the valve 142 cavity to the cylinder 150.

Referring to FIG. 10, the multi cross-sectional view is illustrated. Beginning on the left side of the figure, the cylinder 148 contains piston 126. Channel 180 opens into cylinder 148. It can be seen that channel 180 passes through the valve 140 cavity at the high side (i.e., the high pressure side of a solenoid valve). However, in other embodiments, it is equally possible to configure the cylinders 148 and 150 to be directly in communication with the low side (i.e., the low pressure side of a solenoid valve). A suitable hydraulic system only need to be configured such that it is possible to control the transfer of hydraulic fluid from a high pressure cylinder to a low pressure cylinder. Moving right, the channel 180 intersects the vertical channel 184. A plug is placed in channel 184 to prevent leakage of hydraulic fluid. The horizontal channel 178 intersects the vertical channel 184 at ninety degrees to the channel 180. The channel 178 leads to the valve 142 cavity at the low side of the valve piston (i.e., the low pressure side of a solenoid valve). The high side of the valve 142 cavity is shown connecting with a portion of the horizontal channel 182. The channel 182 leads into the cylinder 150, containing piston 134. The above describes one of two pathways for hydraulic fluid to travel between cylinders 148 and 150. A second pathway is described below.

Figure 11:
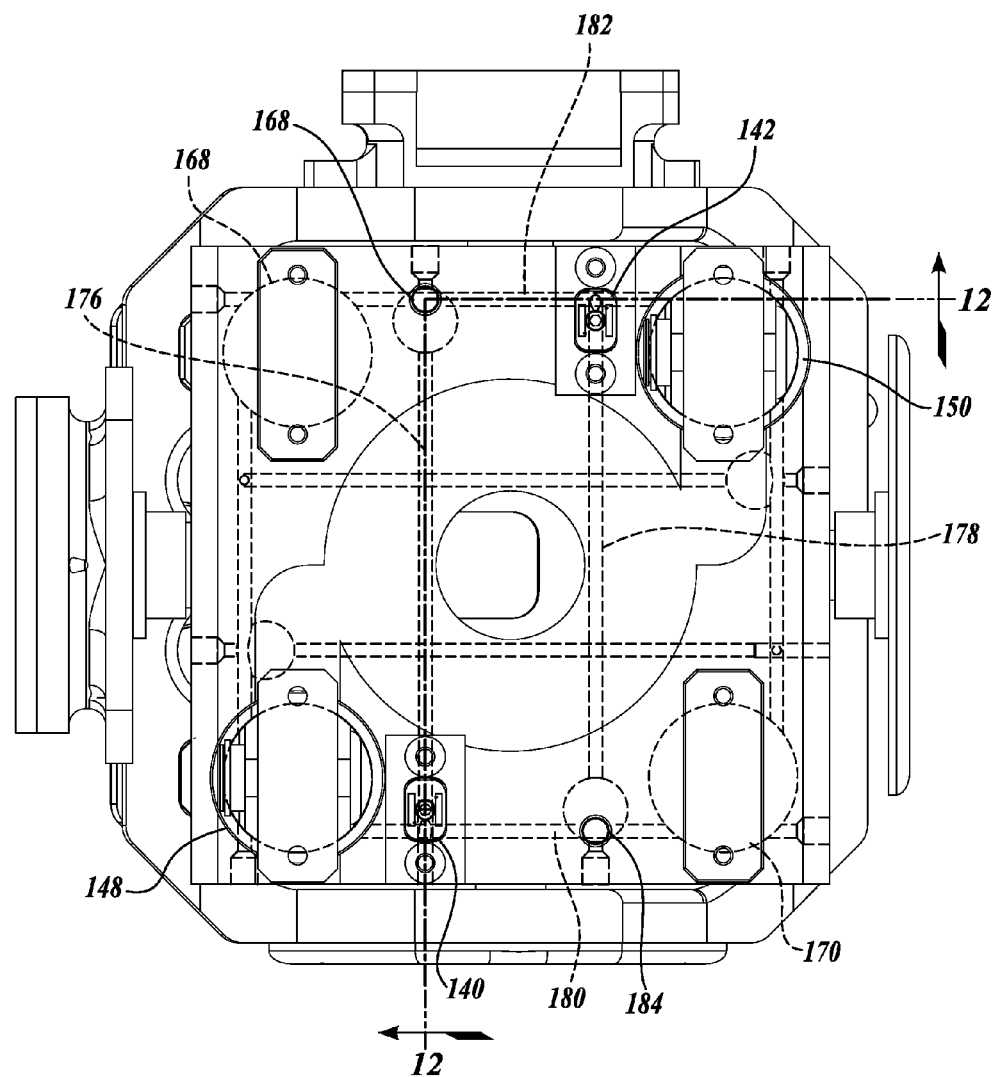
FIG. 11 is a diagrammatical illustration of a top plan view of a hydraulic alignment device with a top plate removed to show the internal hydraulic fluid channels.

Referring to FIG. 11, a cross-sectional view will be taken along the cavity of valve 140, the horizontal channel 176, the vertical channel 168, the horizontal channel 182, the cavity of valve 142, and the cylinder 150.

Figure 12:
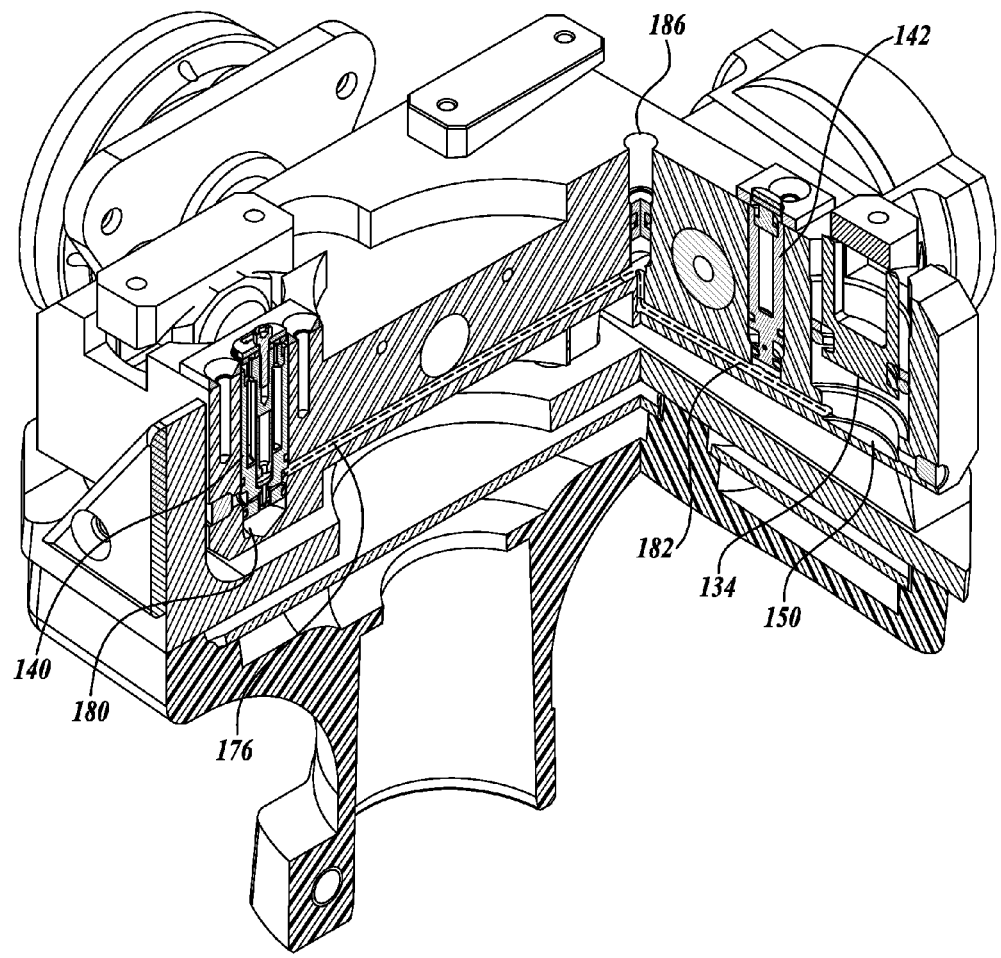
FIG. 12 is a diagrammatical illustration of a perspective multi cross-sectional view of the hydraulic alignment device of FIG. 11.

Referring to FIG. 12, starting on the left side of the figure, the channel 180, which is also shown in FIG. 10, enters the high side of the piston of valve 140. The horizontal channel 176 connects the low side of the piston of the valve 140 to the vertical channel 186. Vertical channel 186 may be plugged to prevent the leakage of hydraulic fluid. The vertical channel 186 connects the horizontal channel 176 to the horizontal channel 182, which is also shown in FIG. 10. The channel 182 passes on the high side of the piston of valve 142, and then opens into the cylinder 150, as described with reference to FIG. 10. As mentioned before, the hydraulic system of channels pertaining to cylinders 168 and 170 is similarly formed, except for being inverted on the middle block 108.

Figure 13:
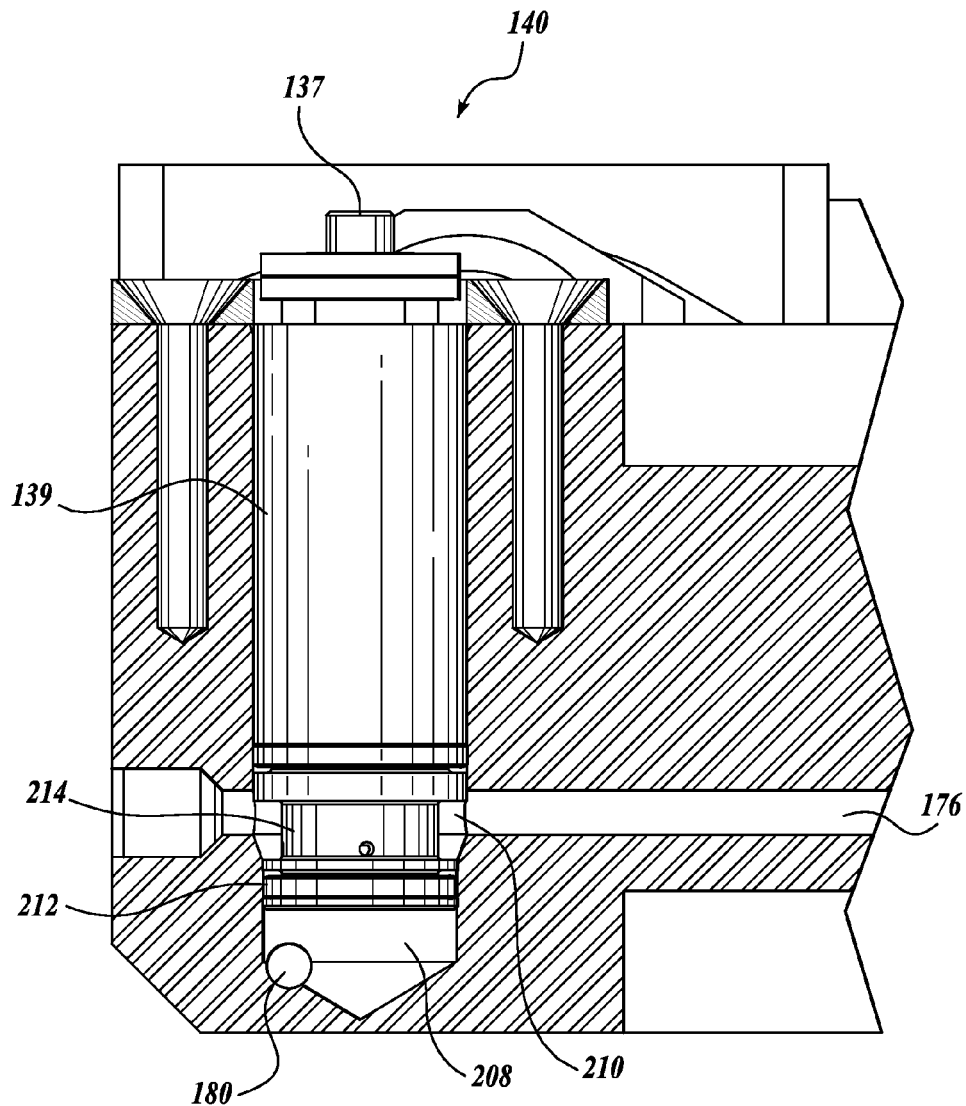
FIG. 13 is a detailed view of a valve in the hydraulic fluid channels in accordance with one embodiment of the present invention.

Referring to FIG. 13, a cross-sectional illustration showing the details of a representative valve 140 is illustrated. The valve includes a solenoid 139. The solenoid includes an electrical contact 137. In one embodiment, a solenoid valve uses a piston or diaphragm to prevent the passage of fluid through the valve. The piston is held against a seat by equalizing both sides of the piston with the high pressure fluid. In one embodiment, when the solenoid is energized, the solenoid converts electrical current into magnetic force to move an armature. The armature allows fluid on the high pressure side of the piston to enter the low pressure side of the piston. The high pressure fluid can now push against the piston compressing a spring, thus allowing high pressure fluid to flow. The hydraulic systems are configured with two solenoid valves because either one of the pair of cylinders may see high pressure. Depending on which cylinder has the high pressure determines which of the two valves to operate to allow transfer of the fluid. Normally, the second valve remains closed when the other valve opens. The volume of hydraulic fluid remains constant in the system so that the hydraulic fluid removed from one cylinder is used to fill the second cylinder.

Figure 15:
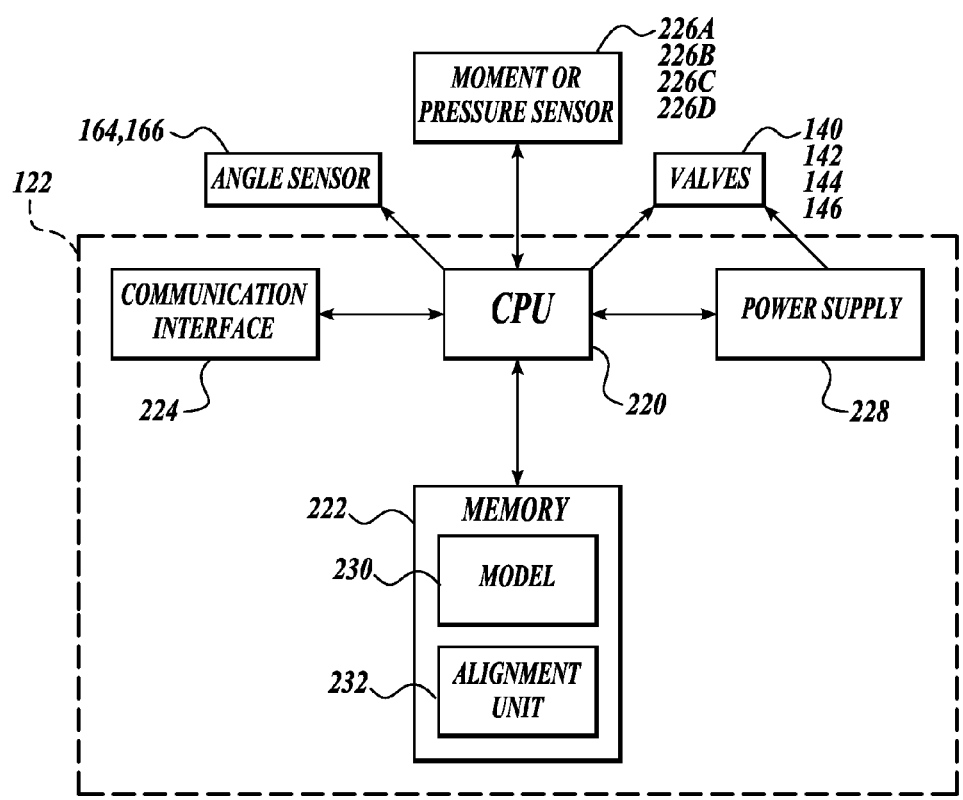
FIG. 15 is a schematic of a control scheme for the hydraulic alignment device in accordance with one embodiment of the present invention.

Referring to FIG. 15, a schematic of the electronics of the hydraulic alignment device 104 is illustrated. The hydraulic alignment device 104 includes a printed circuit board 122. The printed circuit board includes a central processing unit 222. The printed circuit board includes a power supply 228. The printed circuit board 122 includes a memory 222. The memory 222 may be used to store a model of alignment 230 and an alignment unit 232 that compares the model of alignment 230 with real-time data gathered from the moment or pressure sensors 126A-D. The CPU 220 may communicate externally through a communication interface 224. Any communication interface capable of wireless or non-wireless communication is suitable. The CPU 220 receives inputs from the moment or pressure sensors 226A-D. The CPU 220 uses the alignment unit 232 to compare the moment or pressure readings with a model 230. Depending on the readings, the CPU determines whether the prosthesis is unbalanced and needs alignment and which of valves 140, 142, 144, and 146 to open to change the angles of either or both of the top plate 106 or bottom plate 110. The power supply 228 powers the CPU 220 and also provides electrical current to operate the solenoid valves 140, 142, 144, and 146, and the various angle, pressure or moment sensors 226A-D.

Figure 16:
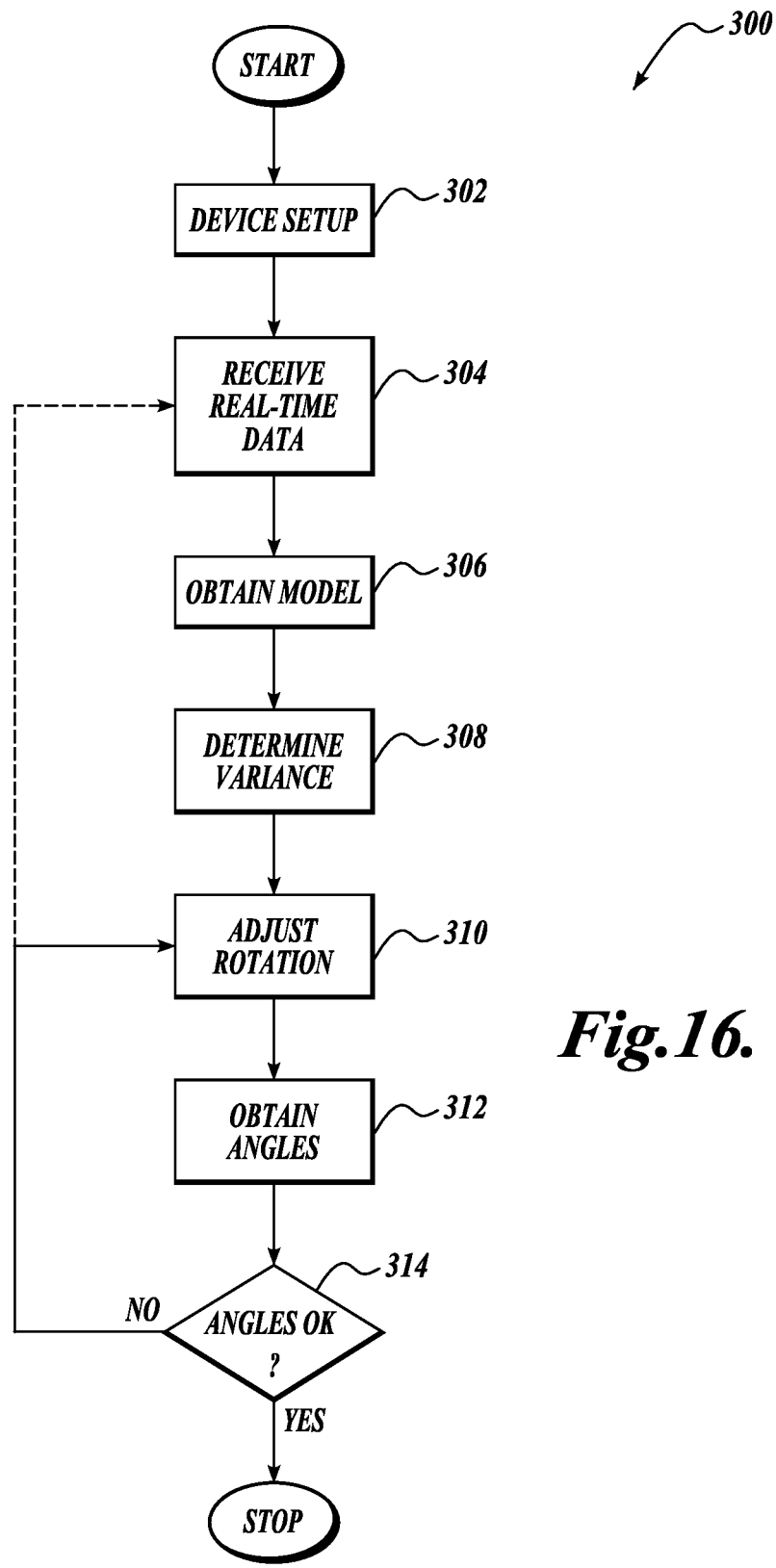
FIG. 16 is a flow diagram of a method to automatically align a prosthesis with the hydraulic alignment device in accordance with one embodiment of the present invention.

Referring to FIG. 16, a flow diagram is illustrated of a method for aligning a prosthesis in real-time while a lower limb amputee patient wearing a prosthesis is walking. The method includes block 302 for device set-up. In the device set-up, the hydraulic alignment device 104 may be programmed with particular instructions, such as a particular model 230, the alignment unit 232, having specific instructions of how the moment or pressure data reading is used and at what limits to open or close valves to change angles. From block 302, the method enters block 304. In block 304, it is assumed that the hydraulic alignment device 104 has been attached to a lower-limb prosthesis. For example, the hydraulic alignment device 104 provides holes on the upper plate 106 to attach to a bottom of a prosthesis socket. The bottom case 124 includes a coupling 124 to connect to a shank and foot. The hydraulic alignment device 104 may be turned on, and the patient uses the prosthesis in the normal manner. During each step with the prosthesis, the pressure and/or moment sensors 226A-D measures the pressures and/or moments and are either stored in memory 222 or used by the CPU 222.

Figure 17:
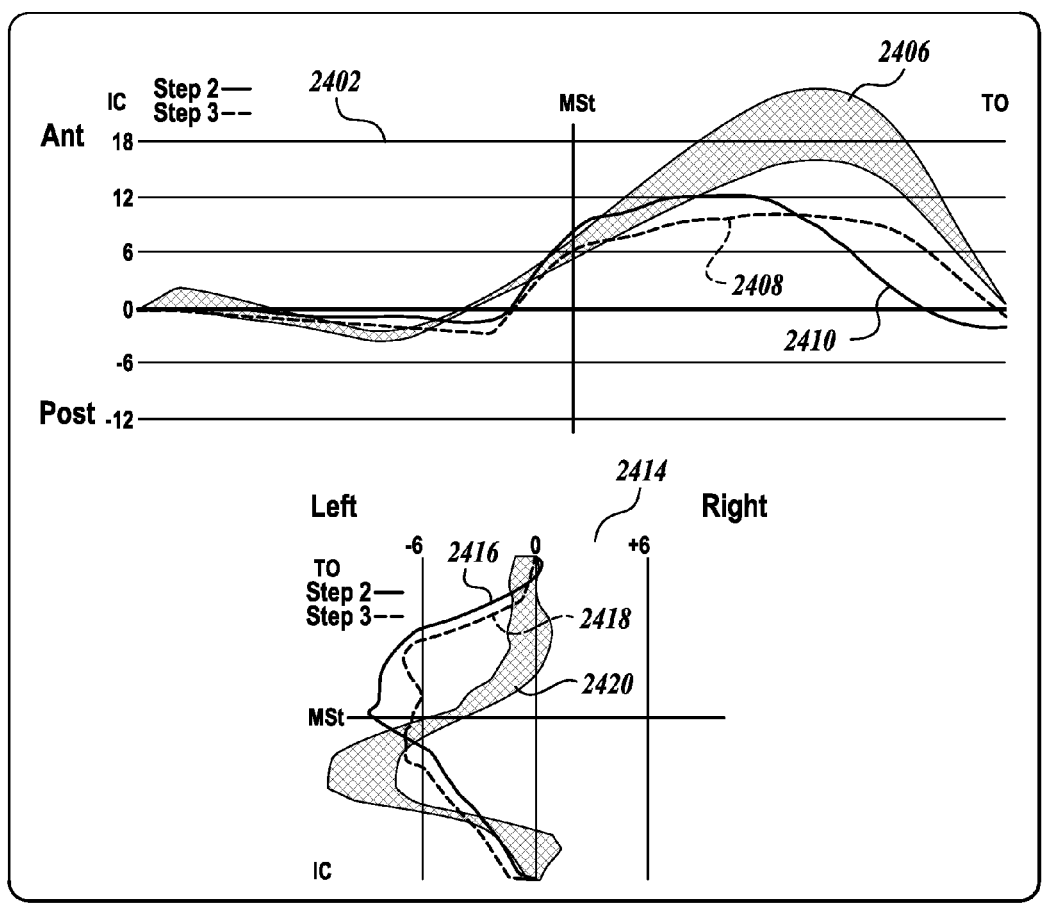
FIG. 17 is a graphical representation of a model compared to measured moment data in accordance with one embodiment of the present invention.

From block 304, the method enters block 306. In block 306, the method obtains a model of alignment. The relationships between the pressures or moments and a correctly balanced or aligned prosthesis are known prior the amputee using the hydraulic device 104 and these relationships are stored in memory 222 as the "model" 230. In one embodiment, the model 230 is derived from a training data set gathered from prosthesis wearers wearing a prosthesis known to be in good alignment or balance. In one embodiment, an ideal spatial alignment defines a characteristic curve or sets of curves of moments in the coronal (right/left) and sagittal (anterior/posterior) planes, plotted from the time a prosthesis foot makes initial contact (IC) with the ground through the time of the toe off (TO) from the ground. The moment sensor 100 may be used to gather the moment information to first create the model. The moment sensor 100 is placed on the prosthesis between socket 20 and shank 60 to measure the moments experienced at the socket 20. The moment sensor 109 gathers moment information that tends to bend the prosthesis either to the left or right (in the coronal plane), or forward or backward (in the sagittal plane) as the prosthesis is used to walk on the ground. The moment sensor 101 includes four sets of strain gauges placed along the sides of four beams connected to a pylori that experiences the forces from the socket since the pylori connects to the shank, which leads to the foot. As the amputee steps with the prosthesis, the moments experienced at the socket are recorded. A model 230 is derived from a set of training data that describe the moments of amputees with properly aligned prosthesis. Referring to FIG. 17, a graphical representation of a model is illustrated by the shaded areas 2406 and 2420 denoting the acceptable range of moments for balance in the anterior/posterior (sagittal) plane 2402 and the right/left (coronal) plane 2414. Moments are plotted for two steps in both the coronal and sagittal planes from the time of initial contact (IC) of the foot to the toe off (TO) from the ground. As shown, the moments represented by curves 2408 and 2410 in the sagittal plane and the moments represented by curves 2416 and 2418 in the coronal plane are not entirely on top of the model. This indicates a need to correct the alignment. One embodiment for deriving a model is by using a training data set collected from a plurality of lower limb amputees with known stabilities. After testing numerous ideally fitted prostheses, the data is collected and used to create the model 230. Statistical methods are known for creating models that describe the ideal behavior from large amounts of data. Another simplified method is to collect moment data from the patient with a prosthesis that is ideally fitted to the patient and with which the patient can walk stably. This moment data then becomes the standard to which the prosthesis must conform when encountering difficult terrain.

From block 306, the method enters block 308. In block 308, the CPU 220 uses the alignment unit 232, the model 230 and the real-time moment and/or pressure data to make decisions concerning whether the prosthesis needs to be aligned. The alignment unit 232 may be used to determine whether the pressures or moments measured in real-time fit the model and so is a properly aligned prosthesis, or if the real-time data does not fit the model, the deviations or the variance from the model can be calculated and converted to degrees of angulation needed to bring the real-time moment and/or pressure data closer to the model. For example, if the wearer is walking sideways along an incline, the natural tendency of the prosthesis is to turn outward to assume an alignment perpendicular to the incline. This increases the moments experienced at the prosthesis socket. The hydraulic alignment device 104 can measures moments or pressures placed on the prosthesis socket with each step and compare the moments or pressures to the model and is able to correct the spatial alignment to move the center of support more toward the center of gravity of the body to reduce the pressures or moments. From block 308, the method enters block 310.

Block 310 is for adjusting the rotation of the top plate 106 and the bottom plate 110 to achieve the desired angles so that the prosthesis is aligned. For this purpose, the relationships between the variations of the real-time moment and/or pressure data to the model 230 and the angles required to bring the real-time moment and/or pressure data closer to the model are stored in the alignment unit 232, either in a "look-up" table or in the form of an equation. The alignment unit 232 can provide the angle in both the sagittal and coronal planes that should result in the real-time moment and/or pressure data being within the model in both planes. The alignment unit 232 also stores the relationships between the angles and the number of pulses needed for the valves 140, 142, 144, and 146 to operate so as to achieve the desired angle in both planes. The alignment unit 232 can provide the number of pulses and the CPU 222 can command the valves the appropriate number of pulses to drive the hydraulic device 104 to move the top plate 106 and the bottom plate 110 to the desired angles. From block 310, the method enters block 312.

In block 312, a measure of the actual angles are obtained from the angle sensors 164, 166 and compared to the desired angles. In block 314, the alignment unit 232 determines whether the actual angles read using the angle sensors 164 and 166 correspond to the desired angles within perhaps a tolerance. If the alignment unit 232 determines that the actual angles correspond to the desired angles within a tolerance, the method terminates for this one instance. For example, the method may be executed at each step. If the alignment unit 232 determines that the actual angles do not correspond to the desired angles within a tolerance, the method returns to block 310 and performs another adjustment of rotation by calculating one or more pulses to make up for the difference between the measured actual angle and the desired angle. The relationships between the angular difference and the number of pulses needed to drive the plates to make up for the difference is stored in the alignment unit 232. The CPU then sends to the appropriate valves the calculated number of pulses. After adjustment, the alignment unit 232 again compares the actual angles measured by the angle sensors 164 and 166 and again compares the actual angles with the desired angles and determines whether more rotation is required. An alternative, if the angles are not okay, is to return to block 304 to receive new real-time data concerning the pressures and/or moments to determine the variance between the real-time moment or pressure data and the model and decide whether the desired angles have changed.

While illustrative embodiments have been illustrated and described, it will be appreciated that various changes can be made therein without departing from the spirit and scope of the invention. For example, while an embodiment is illustrated having the top plate 106, the middle block 108, and the bottom plate 110 to achieve pivoting in two axes, it is possible to have other configurations, such as having two blocks (i.e., an upper and lower block that pivot in orthogonal directions to one another). In this alternative embodiment, a hydraulic system comprising a pair of cylinders, valves and pistons would be placed in each one of the upper and lower block. In this case, the pivot members are the upper and lower blocks. Each block includes a major surface separated by a thickness suitable to contain a hydraulic system as described above. Having a single middle block and two plates may be advantageous because the two hydraulic systems are placed within one block, saving on space. In the case of two blocks, each block would only contain a single hydraulic system. However, it may be possible to have a single block having two hydraulic systems therein and only one plate, thus saving on space.

The invention claimed is:

1. A method for aligning a prosthesis, comprising:
    attaching a hydraulic device to a prosthesis;
    receiving pressures or moments from sensors as a lower limb amputee walks using the prosthesis, the prosthesis comprises an aligned prosthesis socket described by a first true angle in a first plane and a second true angle in a second plane orthogonal to the first plane;
    comparing the pressures or moments to a model, the model describes the relationships between pressures or moments to first and second angles of an optimally aligned prosthesis;
    obtaining the variance between the received pressures or moments and the model;
    converting the variance into a desired angle in the first plane and a desired angle in the second plane, the desired angles are calculated to reduce the variance between the received pressures or moments and the model; and
    transferring hydraulic fluid between a first pair of two diagonally placed cylinders with respect to a first axis of rotation to cause angular motion in the first plane, and transferring hydraulic fluid between a second pair of two diagonally placed cylinders with respect to a second axis of rotation to cause angular motion in the second plane to bring the true angles closer to the desired angles, wherein each cylinder receives a piston therein, wherein each piston travels along a cam surface, and wherein each cam surface provides movement of the piston such that the force applied to the piston is parallel to the cylinder and maintains a constant volume of fluid between opposing cylinders.

2. The method of claim 1, wherein a driving force to transfer the hydraulic fluid is provided by the force of the weight being supported by the prosthesis.

3. The method of claim 1, further comprising sensing the true angles, and comparing the true angles to the desired angles.

4. The method of claim 1, wherein the hydraulic device remains rigid when no transfer of fluid is occurring.

5. The method of claim 1, wherein the hydraulic device pivots in the first plane when hydraulic fluid is transferred from a first cylinder to a second cylinder and pivots in the second plane when hydraulic fluid is transferred from a third cylinder to a fourth cylinder.

6. A method for changing the alignment of a lower limb prosthesis, comprising:
    providing a lower limb prosthesis with a hydraulic device having a first plate that pivots in a first plane and a second plate that pivots in a second plane orthogonal to the first plane, the hydraulic device comprising a pair of two diagonally placed cylinders with respect to a first axis of rotation, wherein each cylinder receives a piston therein, wherein each piston travels along a cam surface, and wherein each cam surface provides movement of the piston such that the force applied to the piston is parallel to the cylinder and maintains a constant volume of fluid between opposing cylinders;

transferring hydraulic fluid between the first pair of two diagonally placed cylinders to cause angular motion in the first plane;

closing a distance between a first side of the first plate and a first side of the second plate when the hydraulic fluid is transferred between the first pair of two diagonally placed cylinders; and expanding a distance between a second side of the first plate and a second side of the second plate when the hydraulic fluid is transferred between the first pair of two diagonally placed cylinders.

7. The method of claim 6, further comprising transferring hydraulic fluid between a second pair of two diagonally placed cylinders with respect to a second axis of rotation to cause angular motion in the second plane; closing a distance between a third side of the first plate and a third side of the second plate when the hydraulic fluid is transferred between the second pair of two diagonally placed cylinders; and expanding a distance between a fourth side of the first plate and a fourth side of the second plate when the hydraulic fluid is transferred between the second pair of two diagonally placed cylinders.

* * * * *